US 6,528,287 B2

(12) United States Patent
Tomycz

(10) Patent No.: US 6,528,287 B2
(45) Date of Patent: Mar. 4, 2003

(54) RECOMBINANT HUMAN SERUM TRANSFERRINS CONTAINING PEPTIDES FOR INDUCING APOPTOSIS IN HIV-1 INFECTED CELLS

(76) Inventor: Nestor D. Tomycz, 519 Cabot Mail Center, Cambridge, MA (US) 02138

( * ) Notice: Subject to any disclaimer, the term of this patent is extended or adjusted under 35 U.S.C. 154(b) by 0 days.

(21) Appl. No.: 09/782,977

(22) Filed: Feb. 13, 2001

(65) Prior Publication Data

US 2002/0146794 A1 Oct. 10, 2002

(51) Int. Cl.$^7$ .................... C12P 21/04; C12Q 1/70; A61K 38/00; A01N 43/04
(52) U.S. Cl. .................... 435/69.7; 435/5; 530/324; 514/44
(58) Field of Search ............... 435/5, 69.7; 530/324; 514/44

Primary Examiner—Hankyel T. Park
(74) Attorney, Agent, or Firm—Michael Bak-Boychuk

(57) ABSTRACT

A mammalian protein, like the human serum transferrin (HST), is modified with an inserted peptide sequence flanked at both ends by cleavage sites. The peptide insert contains a motif known to induce apoptosis in cells and the cleavage sites are specific for the viral protease of HIV-1. The delivery of such recombinant transferrin into an HIV-1 infected cell results in the release of the peptide which then induces apoptosis. The peptide is inserted into surface exposed loops of the N-terminal lobe of the HST containing the RGD motif flanked by two modified p17/p24 HIV-1 protease cleavage sites. When delivered to the infected cell the cleavage of the loop inserted sequences by the HIV-1 protease results in the release of the central RGD-containing peptide sequences. Peptides containing the RGD motif (arginine, glycine, aspartic acid) have been shown to induce cell apoptosis even in small concentrations.

14 Claims, 5 Drawing Sheets

Natural p17/p24 Cleavage Site: VSQNY*PIVL

Modified p17/p24 Cleavage Site: VSQNY*VIVL

Figure 1:
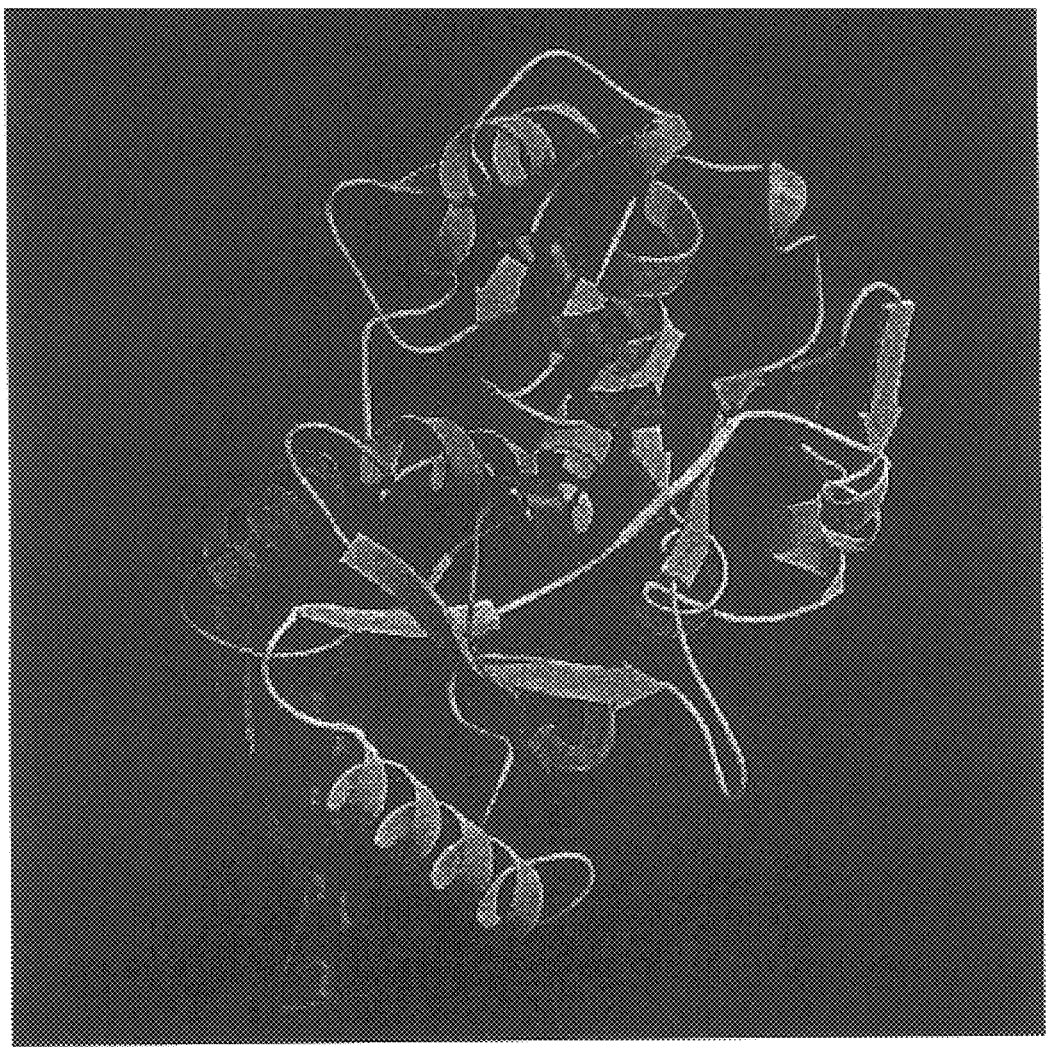
Figure 2:
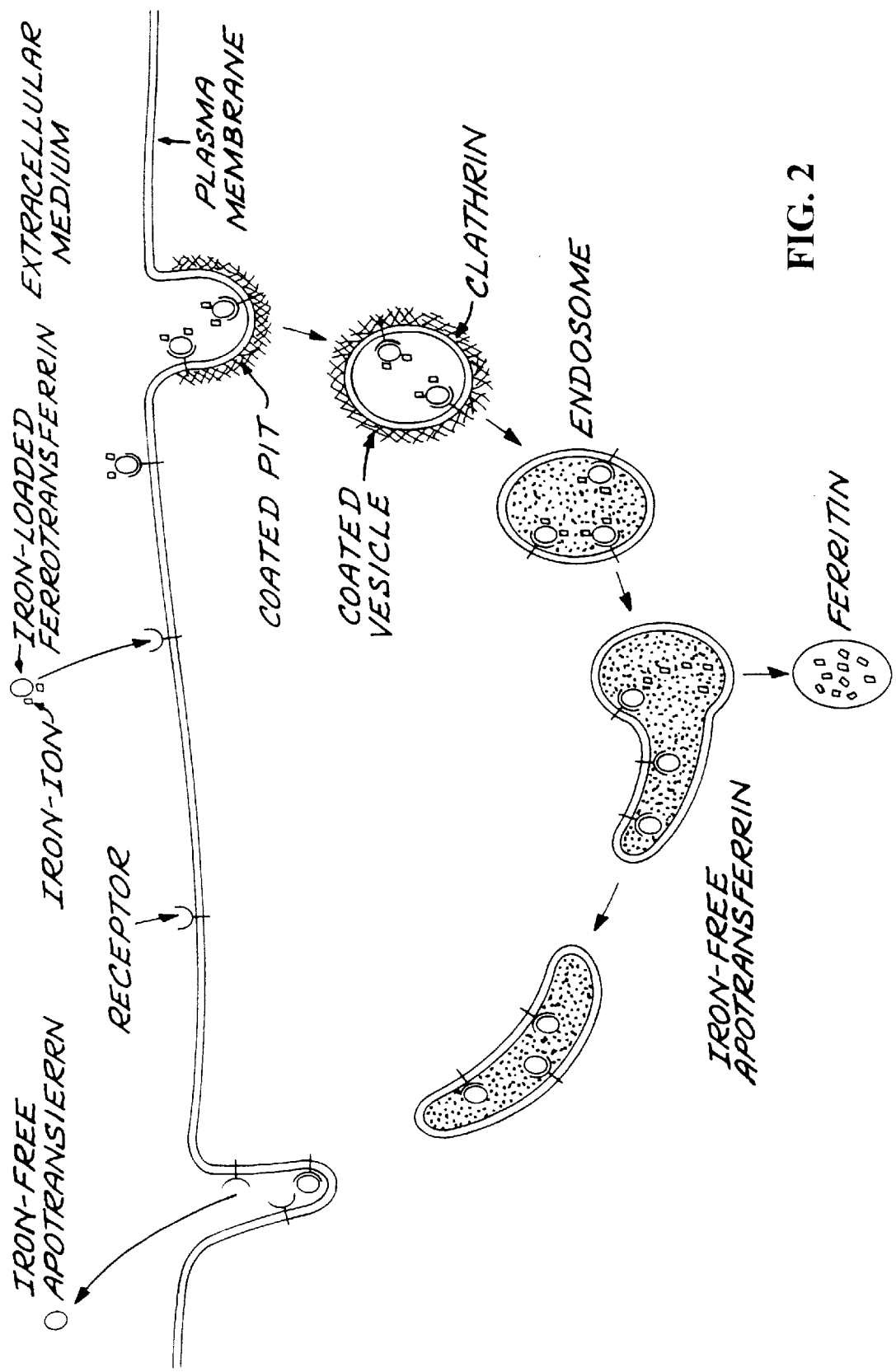
Figure 3:
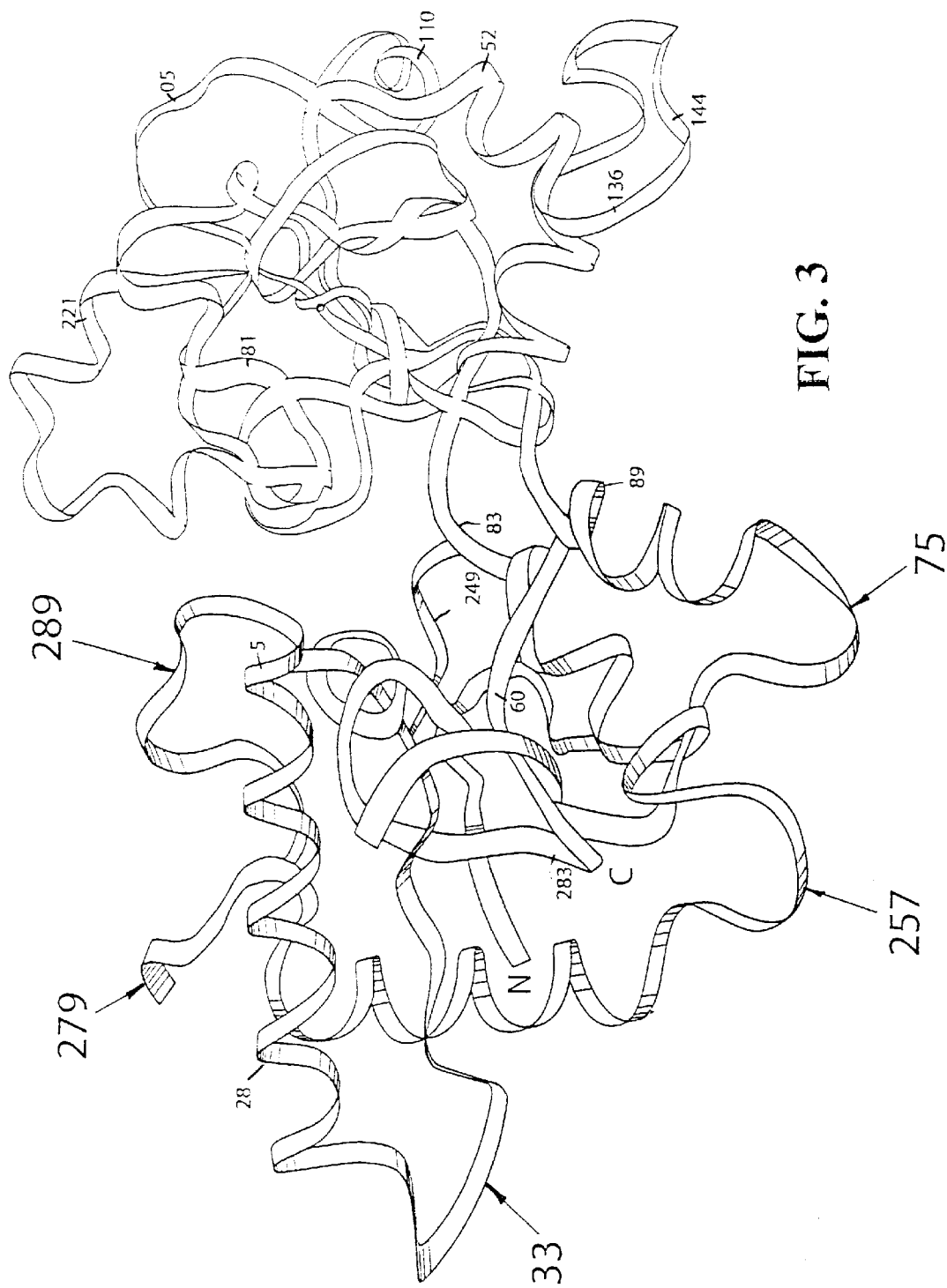
Figure 4:
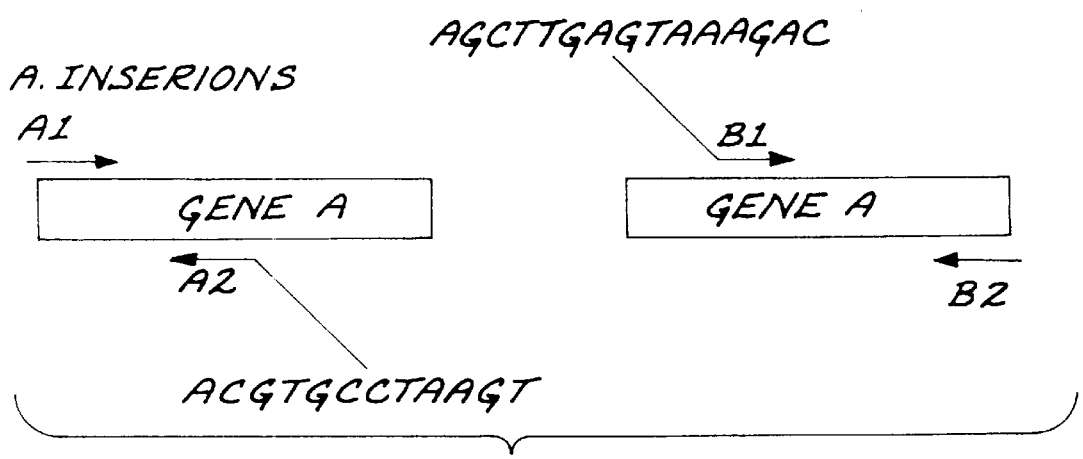
Figure 6:
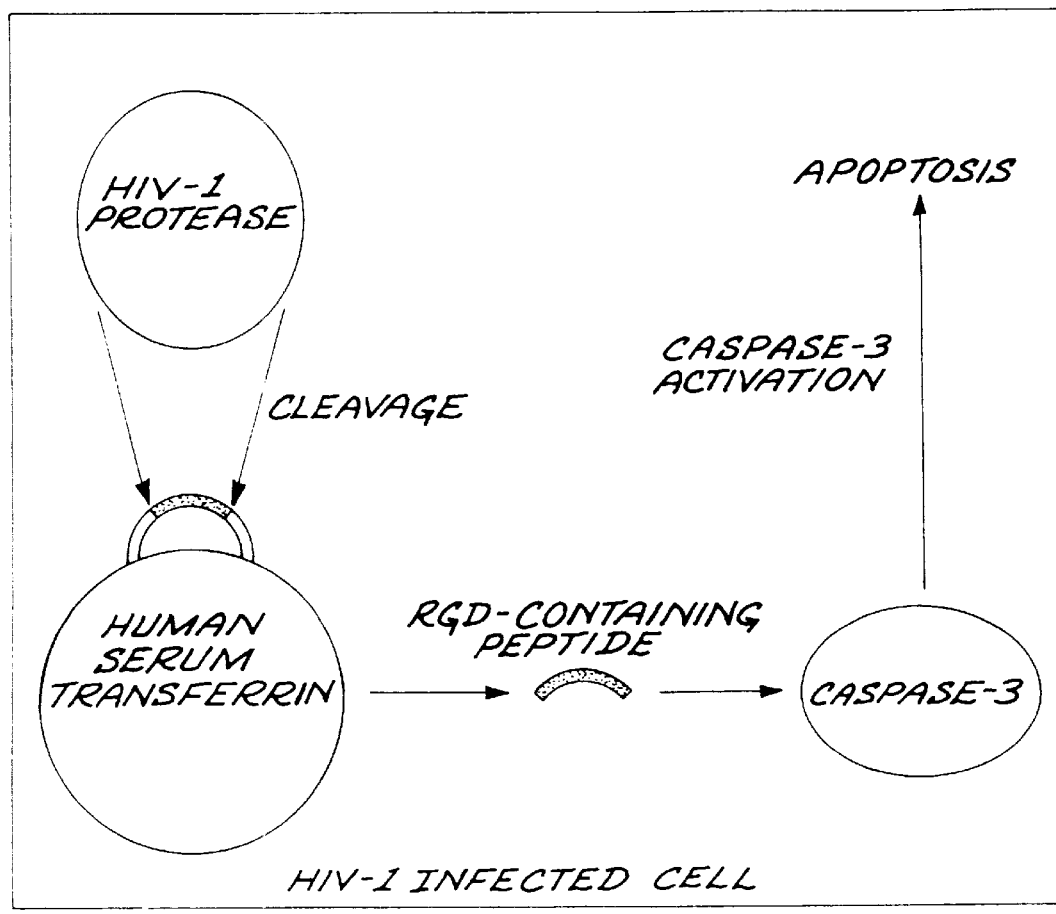

* indicates site of HIV-1 protease cleavage

Peptide Mut1: VSQNY*VIVLRGDVSQNY*VIVL
Peptide Mut2: VSQNY*VIVLRGDSVSQNY*VIVL
Peptide Mut3: VSQNY*VIVLGRGDNPVSQNY*VIVL
Peptide Mut4: VSQNY*VIVLGRGDSPVSQNY*VIVL Cleavage of Mut1-4 at * releases an RGD-containing peptide which is stabilized due to a N-terminal valine (V):

Figure 5

RECOMBINANT HUMAN SERUM TRANSFERRINS CONTAINING PEPTIDES FOR INDUCING APOPTOSIS IN HIV-1 INFECTED CELLS

BACKGROUND OF THE INVENTION

1. Field of the Invention

The present invention relates to biological structures designed to induce apoptosis in HIV-1 infected cells, and more specifically to recombinant human serum transferrins designed to introduce apoptosis-inducing peptides into HIV-1 infected cells.

2. Description of the Prior Art

The preservation of equilibrium in a multicellular organism, the process of homeostasis, requires a delicate balance between cell proliferation and cell death. In a well developed, adult organism the maintenance and renewal of many specialized cell lines is a matter of continuing importance. Therefore, cell proliferation and in particular its tight checks and balances necessary for optimal adult health has been a process of keen interest to those involved in biological research. Accordingly, the study of infectious diseases and more recently the focused inspection of mechanisms associated with cancer have followed these adult self-preservation paths, expanding our knowledge of the many factors involved in cell proliferation—where some of the more recent research has elucidated the importance of growth factors, proto-oncogenes, and tumor suppressors such as p53.

Over the whole life cycle the viability of an organism is maintained by a continuous balance between cell proliferation and cell death by necrosis or apoptosis. While the necessity of cell suicide in an organized biological system has been well appreciated, it is only recently that it was given substantial research attention as a therapeutic mechanism.

For example, the study of Acquired Immune Deficiency Syndrome (AIDS) caused by the Human Immunodeficiency Virus (HIV) has revealed that uninfected CD4+ T cells are induced to undergo apoptosis by adjacent HIV-infected cells. It appears that the survival strategy of this virus depends in part on causing mass suicide in the ranks of its primary immunological opponent, the T lymphocyte, while remaining concealed in the suicide inducer, the infected cell. See, e.g., Meyaard, L. et al. (1992) *Science* 257:217; Groux, H. et al. (1992) *J. Exp. Med.* 175:331; Banda, N. K. et al. (1992) *J. Exp. Med.* 176:1099. Since apoptosis, unlike necrotic cell death, does not normally evoke inflammation or a strong immune response, this viral stratagem is particularly successful; the disease remains essentially symptom free until opportunistic infections are allowed to take hold as a result of depleted T cell ranks.

The opposing therapeutic stratagems need equal brilliance. Following the clandestine path of this virus, the use of apoptosis induction as a therapeutic tool is attractive as it can avoid potentially harmful inflammatory and immune system responses. The insidious nature of the HIV process, its current prevalence, and its essentially asymptomatic onset are best opposed by equally asymptomatic response mechanisms in any therapeutic regimen. Accordingly, therapeutic mechanisms that induce apoptosis in HIV infected cells are universally desired, and it is one such mechanism that is disclosed herein.

Those in the field will appreciate that recent (1999) estimates by the World Health Organization (WHO) indicate that there are no less than 33.6 million people living with HIV/AIDS. Recently it has been observed and reported that the combination of simultaneous protease and reverse transcriptase inhibitors does not confer resistance to HIV. See Michael, N. and Moore, J. (1999) *Nature Medicine* 5:7, 740–741. The infective nature of this disease offers only somber future statistics. Accordingly, various new drugs to combat this epidemic have been proposed, including those based on cleavage by HIV-1 protease, such as the toxic pro-drugs activated inside the infected cell (the Trojan Horse strategy), peptide drugs and others.

At the same time the study of natural transport proteins has revealed the unique attributes of the human serum transferrin as a delivery mechanism, and its concurrent convenience for recombinant manipulation. For example, U.S. Pat. No. 5,986,067 to Funk et al. (1999) teaches the usefulness of recombinant transferrin proteins as vehicles for metal chelation while Ali, S. A. et al. (1999) *J. Biol. Chem.* 274:34, 24066–24073 describe the insertion of a peptide sequence into the N-terminal lobe of human serum transferrin via cassette mutagenesis and PCR-ligation-PCR mutagenesis techniques.

When Ali et al. inserted a peptide into the N-terminal lobe of human serum transferrin (HST), they demonstrated that the recombinant HST retained its native functions, including mediation of iron transport and uptake into cells. Human serum transferrin is a monomeric glycoprotein that binds tightly and reversibly to two ferric ions together with two bicarbonate co-ions. The roles of HST are 1) the regulation of the availability of free iron in body fluids and 2) mediation of the transport and uptake of iron into cells via receptor-mediated endocytosis. Even though all living cells need iron, only those cells which have high iron requirement (i.e. HIV-infected cells and cancer cells) express large numbers of transferrin receptors. See lacopetta et al. (1982) *Biochem. Biophys. Acta.* 687:204–210. Significantly, HIV-1 replication has been shown to induce up-regulation of HST receptor expression, and therefore HIV-1 infected cells are particularly susceptible to an HST-directed therapy. The use of recombinant human serum transferrin is therefore uniquely suitable for the process disclosed herein.

An essential step in the life cycle of human immunodeficiency virus type-1 (HIV-1) is the processing of the Gag and Gag-Pol polyproteins which is performed by the virus encoded HIV-1 protease. The cleavage of viral polyproteins by HIV-1 protease results in structural and catalytic proteins required for both viral maturation and infection, and therefore HIV-1 protease has been a target of anti-AIDS drugs. See Friedler, A. et al. (1999) *J. Mol. Biol.* 287:93–101. One novel approach that has been recently examined is the use of toxic prodrugs which are cleaved selectively in cells infected by HIV-1—often called the "Trojan Horse" strategy. A chimeric Vpr protein (an auxiliary HIV-1 gene product) which contained at its C-terminus nine HIV-1 protease cleavage sites was shown to completely abolish viral infectivity as cleavage of the chimeric protein interfered with the processing of viral precursor proteins—leading to the production of incompletely processed noninfectious virus particles. See Serio, D. et al. (1997) *Proc. Natl. Acad. Sci. USA* 94:3346–3351. The current invention described herein combines the Trojan Horse strategy with recent knowledge of the existence of peptides which cause cell suicide. The proposed recombinant human serum transferrins would inhibit HIV-1 by acting as competitive substrates for HIV-1 protease and in so doing would also selectively release "cell suicide"0 peptides in the HIV-1 infected cell. Therefore, the proposed invention endeavors to not only inhibit the virulence of HIV-1 but also to eradicate those cells infected by HIV-1.

SUMMARY OF THE INVENTION

Accordingly it is the general purpose and objective of the present invention to design a recombinant mammalian protein directed at seizing the normal process of apoptosis or "cell suicide" as a therapeutic stratagem.

Further objects of the invention are to create various recombinant human serum transferrin proteins containing one of several peptides flanked by two HIV-1 protease cleavage sites and possessing an apoptosis-inducing motif.

Other objectives of the invention are to provide a modification of a protein structure generally functional in basic biological processes whereby the protein modification includes apoptotic peptide segments inserted between cleavage sites selected for a targeted infection.

Yet further objectives of the invention are to create recombinant modifications of a natural transport protein so as to conform it to induce cell apoptosis in an HIV-1 infected cell.

Additional objectives of the invention are to insert an apoptotic mammalian peptide which may be released from the designed recombinant mammalian protein in an infected cell via cleavage by the HIV-1 protease enzyme.

In each of the foregoing objects the invention aims to create such modifications in a way that will not compromise the biological roles of the human serum transferrin protein.

Briefly, these and other objects are accomplished within the present invention by modifying a mammalian protein, like the human serum transferrin (HST) protein, with an inserted peptide sequence flanked at both ends by cleavage sites. The proposed peptide insert contains a motif known to induce apoptosis in cells and the cleavage sites are specific for the viral protease of HIV-1. The delivery of such recombinant transferrin into an HIV-1 infected cell may result in the release of the peptide which can then induce apoptosis.

The peptides designed in accordance with the present invention for insertion into surface exposed loops of the N-terminal lobe of human serum transferrin are: SEQ ID No: 1 VSQNYVIVL<u>RGD</u>VSQNYVIVL SEQ ID No: 2 VSQNYVIVL<u>RGDS</u>VSQNYVIVL SEQ ID No: 3 VSQNYVIVL<u>GRGDNP</u>VSQNYVIVL, SEQ ID No: 4 and VSQNYVIVL<u>GRGDSP</u>VSQNYVIVL. These peptide inserts include in each instance an apoptosis inducing peptide containing the RGD motif (indicated by bold, underlined script) flanked by two modified p17/p24 HIV-1 protease cleavage sites.

When delivered to the infected cell, the cleavage of the loop inserted sequences by the HIV-1 protease results in the release of the central RGD-containing peptide sequences. Peptides containing the RGD motif (arginine, glycine, aspartic acid) have been recently shown to induce cell apoptosis even in small concentrations (as low as 250 micromolar). See Buckley, C. et al. (1999) *Nature* 397:534–39. Buckley et al. demonstrates that peptides containing the RGD motif (the minimal sequence required to induce apoptosis was the RGD motif by itself) induced rapid apoptosis in resting ($G_0$) peripheral blood T cells, CD4-positive T-cell lines, leukaemic T-cell lines (Jurkat and Molt-4 cells), B cells transformed by Epstein-Barr virus (LCL cells), and the erythroleukaemic cell line K562. The current hypothesis is that the RGD-containing peptide directly activates caspase-3, the apoptotic point of no return. Caspase-3 is a an apoptotic zymogen whose activation allows it to cleave the inhibitor of caspase-activated DNAase, leading to cell suicide. It is of particular significance to this invention that the RGD peptide motif has been shown to induce apoptosis in CD4-positive T cells, as the CD4-positive T helper cell is the primary target of the lymphotropic HIV virus; see Kuby, J. *Immunology.* 3$^{rd}$ Edition. W. H. Freeman and Co., New York, 1997.

The sequences flanking the RGD-containing peptides (bold, underlined) above are modified p17/p24 HIV-1 protease cleavage sites (VSQNYVIVL). The natural p17/p24 HIV-1 protease cleavage site is VSQNYPIVL, and HIV-1 protease cleaves at the YP junction. The modified p17/p24 HIV-1 protease cleavage sites (VSQNYVIVL) used in the designed peptides have a proline to valine substitution in the P1' position of the cleavage site. This modification was used so that the peptides released following cleavage by HIV-1 protease have a valine (V) N-terminal terminal amino acid which is stabilizing according to the N-end rule; the mammalian N-end rule associates the intracellular half-life of a protein with its N-terminal amino acid. Cleavage of the modified p17/p24 HIV-1 protease cleavage sites occurs at the YV junction, and the substitution of valine for proline has been shown to only have a minor effect on cleavage by HIV-1 protease. See Falnes et al. (1999) *Biochem. J.* 343:199–207. This modification substantially improves the stability of the released apoptosis-inducing peptides so that they are more likely to activate caspase-3 and the cell suicide pathway.

Those in the art will appreciate that human serum transferrin, a monomeric glycoprotein that binds tightly and reversibly to two ferric ions together with two bicarbonate co-ions, regulates the availability of free iron in body fluids, and also mediates the transport and cell uptake of iron by receptor-mediated endocytosis. See Huebers, H. et al. (1981) *Proc. Natl. Acad. Sci.* USA 78:1, 621–625; Jeffrey P. D. et al.(1998) *Biochemistry* 37:13978–13986; Ali, S. A et al. (1999) *J. Biol. Chem.* 274:34, 24066–24073. By this process, the transferrin molecule binds to the transferrin receptor on the membrane of cells and the complex is subsequently enveloped by the cell. Significantly, HIV replication has been shown to induce upregulation of HST receptor expression since HIV-infected cells exhibit a higher need for iron. See Levy, J. A. (1993) *Microbiol. Rev.* 57:183–289. Even more significantly, while conjugating peptides to human serum transferrin has been shown to induce an antibody immune response, hiding peptides within the loops of transferrin has not been associated with detectable antibody production. See Ali et al. (1999) *FEBS Letters* 459:230–232. Thus, human serum tranferrin provides an attractive pathway for the delivery of engineered peptides into HIV-infected cells as it takes advantage of a pre-evolved cell entry mechanism, exercises selectivity for HIV-infected cells which possess a greater number of transferrin receptors, and minimizes immunogenicity which often complicates the use of peptide drugs.

The efficacy of this mechanism is further enhanced by selecting insertion sites that are removed from the transferrin C-terminal lobe, known to be important for iron and bicarbonate binding. The C-terminal lobe of transferrin also possesses the primary sites for HST receptor recognition. See Zak et. al., *J. Biol. Chem.*, 269:10, 7110–7114. Stability of the peptides once released into the cytoplasm is improved by including two modified p17/p24 HIV-1 protease cleavage sites in substitution for the natural p17/p24 cleavage sequence VSQNYPIVL. In this manner the released peptide conforms with the stabilizing N-end rule, and the peptide can be inserted into the N-terminal lobe surface exposed loops of transferrin, which are removed from the iron transport machinery. Surface exposed loops of the HST protein are the chosen targets of peptide insertion due to their flexibility and therefore resulting ability to tolerate insertions without significantly distorting the overall tertiary or three-dimensional spatial structure of the protein. See Finkelstein, A. V. (1997) *Curr. Opin. Struct. Biol.* 7:60–71. Furthermore, surface exposed loops are chosen so that peptide sequences can be exposed to HIV-1 protease recognition and cleavage.

BRIEF DESCRIPTION OF THE DRAWINGS

FIG. 1 shows the x-ray crystal structure of the N-terminal lobe of human serum transferrin (MacGillivray, R. T. et al. (1998) *Biochemistry* 37:7919;

FIG. 2 is a diagrammatic illustration of the delivery of iron by human serum transferrin via receptor-mediated endocytosis;

FIG. 3 is an illustration of a three dimensional structure of the N-terminal lobe of human serum transferrin, as obtained by x-ray crystallography, illustrating the five preferred insertion sites (32–33, 74–75, 256–257, 279–280, 288–289) in the exposed N-terminal loop regions of HST as determined by Ali et al. (1999) *J. Biol. Chem.* 274:34, 24066–24073;

FIG. 4 illustrates schematically the steps in the PCR-ligation-PCR mutagenesis procedure that does not require primers with overlapping complementary sequences, useful to generate insertions in accordance with the present invention (Ali et al. (1995) *Bio Techniques* 22:1060–1062);

FIG. 5 illustrates the natural and modified p17/p24 HIV-1 protease cleavage site as well as the proposed inventive peptides. The modified p17/p24 HIV-1 protease cleavage site has a proline to valine substitution in the P1' position so that the cleaved out peptides have an N-terminal stabilizing valine according to the N-end rule;

FIG. 6 depicts the theoretical sequence of events which leads to the selective eradication of HIV-1 infected cells by using the modified HST constructs described herein.

DETAILED DESCRIPTION OF THE INVENTION

Generally, the present invention provides for the production of recombinant human serum transferrins which contain cleavable apoptotic peptide motifs inserted into surface exposed loops of the HST N-terminal lobe. Large amounts of homogeneous recombinant transferring can be generated through the techniques of recombinant DNA technology. Briefly, the creation of the inventive recombinant transferrins entails the transfection of suitable host cells with the DNA encoding the transferrin, culturing the transfected host cell, and finally recovering the expressed recombinant transferrin. The DNA and amino acid sequence of human serum transferrin has been determined; see Yang, F. et al. (1984) *Proc. Natl. Acad. Sci.* USA 81:2752–2756.

A. The Process of Producing Recombinant Human Serum Transferrin:

Mutagenesis techniques and methods have now advanced to a point where the creation of a protein with any desired amino acid sequence can be achieved with regular predictability. For example, synthesis of gene segments by a construction method from both ends towards the middle has been described in U.S. Pat. No. 5,093,251 issued on March 3, 1992 to Richards et al. generally known as the "cassette method." Central to this and the other current methods is the ability to synthesize DNA oligonucleotides having a particular sequence of nitrogenous bases. These synthetic oligonucleotides are then useful to specifically alter genes in a process known as site-directed mutagenesis in which an oligonucleotide with a desired base alteration is used as a primer in the DNA polymerase-mediated replication of a gene. Despite some mismatched base pairs, the oligonucleotide will hybridize to the wild-type gene, and its extension by a DNA polymerase enzyme will yield the mutated gene. Altered genes can then be used to produce altered or mutated proteins via molecular cloning where the DNA segment coding for the altered protein is inserted into an autonomously replicating DNA molecule, a cloning vector or vehicle.

The resulting vector is then placed into a host organism such as *E. coli* or yeast resulting in the production of large amounts of the DNA segment since the organism possesses the necessary enzymes to replicate the vector. Control sequences that are part of the vector allow the host to produce large quantities of the RNA and protein encoded by that gene.

At the same time, the use of polymerase chain reaction (PCR) developed by Kerry Mullis is also an essential part of modern biochemical research as it allows one to directly amplify a specific segment of DNA. PCR amplification has become important in rapid diagnosis of infectious disease and the detection of mutations that could lead to cancer. PCR is now also widely known as a forensic tool used to amplify the DNA of a single hair or sperm, leading to unambiguous identification of the donor.

PCR involves multiple cycles of DNA denaturation (melting) and synthesis, leading to exponential amplification of a specific gene segment of DNA. Synthetic DNA oligonucleotides called primers are used to flank the gene of interest; only the genetic material flanked by the primers will be specifically amplified by a DNA polymerase. PCR is also useful to generate mutated DNA that contains deletions, insertions or point mutations. For example, insertion of a segment of DNA into a gene can be achieved with the PCR-ligation-PCR mutagenesis technique described by Ali, S. A. and Steinkasserer, (1995) A. *Bio Techniques* 22:1060–1062. Briefly, this procedure requires that one design two sets of primers for PCR that contain the sequence to be inserted. Using the two sets of primers, both halves of the HST gene are amplified separately along with the mutant DNA sequences found on the internal primers. The two amplified halves of HST are then phosphorylated by a kinase which avails them to connection via a ligase enzyme. A final PCR reaction using two external primers which flank the complete gene results in the amplification of the recombinant gene containing the insert, which can lead to a protein with an inserted peptide via expression. Accordingly, the techniques utilized herein are well appreciated by those skilled in the art.

B. The Human Serum Transferrin Insertion Site Candidates:

Recombinant human serum transferrin has been used successfully in the recent past as a vehicle for peptides in which the mutant human transferrin: 1. retains its native function; and 2. the inserted peptide is surface exposed. See Ali, S. et al. (1999) *J. Biol. Chem.*, 274:34, 24066–24073. This surface exposure is best understood by reference to the image shown in FIG. 3, obtained by computer analysis of the x-ray crystal three dimensional structure of the N-terminal lobe of human serum transferrin. In this illustration the preferred insertion sites are identified by the designations I, II, III, IV and V, respectively corresponding to codons 32–33, 74–75, 256–257, 279–280 and 288–289. These sites are known as potential insertion sites for peptides and have been so identified in the above reference.

Each of these particular sites are in the exposed loop regions selected for their distance from residues known to be important for iron and bicarbonate binding, hinge function, and transferrin receptor interaction, all shown to be primarily at the C-terminal lobe of HST. See Steinkasserer et al., supra. Moreover, prior research has shown that insertion of peptides into the exposed loops of globular proteins is generally well tolerated without altering biological function, and such insertions do not significantly affect the stability and folding rates of the protein. See, respectively, Finkelstein, A. V. (1997) *J. Mol. Biology* 7:60–71 and Ladurner, A. G. and Fersht, A. R. (1997) *J. Mol. Biology* 273:330–337. Thus the foregoing site selections in the exposed loops of the N-terminal lobe of the HST protein are particularly suitable for the peptide insertion described herein.

C. Membrane Targeting of the Recombinant Human Serum Transferrins:

Although there is some HIV-1 protease in the cytosol, most HIV-1 protease activity occurs at the site of viral budding; therefore, the HIV-1 protease concentration is likely to be highest at the plasma membrane. See Falnes, P. et al. (1999) *Biochem. J.* 343:199–207. HIV-1 protease cleavage of the proposed recombinant human serum transferrins may be enhanced by the addition of a membrane-targeting signal. Thus, the addition of a ten amino acid membrane targeting signal to the C-terminus of the designed recombinant human serum transferrins is proposed. The $p21^{ras}$ proteins are targeted to the plasma membrane by plasma membrane localization sequences found at their C-terminus. One part of the targeting sequence is an intact CAAX (C=cysteine, A=aliphatic, X=any amino acid) motif at the C-terminus of the protein. The second part of the targeting sequence in the case of $p21^{H-ras}$ is a cysteine palmitoylation site. See Hancock, J. F. et al. (1991) *The EMBO Journal* 10:13 4033–4039. Hancock et al. attached such C-terminal amino acids of $p21^{H-ras}$ to the C-terminus of protein A and cytosolic GAP protein, and they showed that the chimeric proteins localized to the plasma membrane. Thus, in accordance with the present invention the designed human serum transferring are further modified with C-terminal membrane target signals of the type found in $p21^{H-ras}$. More specifically, the membrane targeting signal chosen for the recombinant human serum transferrins found herein consists of the last C-terminal ten amino acids of $p21^{H-ras}$ which contains two cysteine palmitoylation sites plus a CAAX motif.

D. Construction of the Inventive Recombinant HST:

It is generally known that human serum transferrin is a protein and the production of recombinant human serum transferrins begins at the level of DNA. Deoxyribonucleic acid (DNA) encodes protein sequence with codons where a codon consists of three DNA base pairs which together code for one particular amino acid. In this way, a stretch of DNA encodes a protein, which is a polymer of amino acids. Therefore, the manipulation of DNA permits one to design the genetic blueprint of any protein. The construction of the proposed recombinant human serum transferrin begins with obtaining the gene for normal human serum transferrin inside a plasmid, which is a closed circle of DNA.

The plasmid TFR27A contains the HST gene and can be obtained from American Type Culture Collection (A.T.C.C., Rockville, Md., catalog no. 53106). The HST gene in this plasmid is then be amplified via the known polymerase chain reaction (PCR) by using primers (oligonucleotides) containing restriction sites. Polymerase chain reaction (PCR) is a standard molecular biology technique that permits one to exponentially amplify a specific piece of DNA, such as a gene. PCR requires the use of DNA primers that have sequences complementary to regions flanking the target. DNA primers are single-stranded pieces of DNA which are synthesized and sold by many commercial laboratories.

E. Selection of Peptide Insertion Sites:

The optimal peptide insertion sites in the human serum transferrin molecule have been suggested and tested. See Ali et al. (1999) *J. Biol. Chem.* 274:34, 24066–24073. These five candidate insertion sites in human serum transferrin (HST) are after codons 1) 32–33, 2) 74–75, 3) 256–257, 4) 279–280, 5) 288–289—where peptide insertion would presumably be least detrimental to biological activity. These sites were chosen for their location within surface exposed loops and for their distance from the C-terminal lobe of HST, which confers HST with receptor recognition and iron/bicarbonate binding functionality. The numbers (32–33, 74–75, 256–257, 279–280, 288–289) represent codons in the DNA sequence of HST. A codon consists of three DNA base pairs which together code for one particular amino acid. The designed peptides would be inserted into the five candidate sites in the N-terminal lobe of human serum transferrin by using the same general methodology employed by Steinkasserer et al. who pioneered the insertion of peptides into surface exposed loops of HST. See Ali et al. (1999) *J. Biol. Chem.* 274:34, 24066–24073.

SPECIFIC EXAMPLES OF THE INSERTED PEPTIDE

The following inventive peptides are proposed for inducing apoptosis in HIV-1 infected cells, designated by a mutation nomenclature for convenience:

Example 1
VSQNYVIVLRGDVSQNYVIVL (Mut. 1),

Example 2
VSQNYVIVLRGDSVSQNYVIVL (Mut. 2),

Example 3
VSQNYVIVLGRGDNPVSQNYVIVL (Mut. 3) and

Example 4
VSQNYVIVLGRGDSPVSQNYVIVL (Mut. 4).

Each of the foregoing may be inserted at the N-terminal lobe sites hereinbefore described.

F. Subcloning of the HST Gene into the Baculovirus Protein Expression System:

The native HST gene would be subcloned into a baculovirus expression vector system (BEVS). The baculovirus expression vector system is now commonly used for expressing recombinant mammalian proteins. See O'Reilly, D. R., Miller, L. K., and Luckow, V. A. (1994) *Baculovirus Expression Vectors: A Laboratory Manual,* Oxford Univ. Press, Oxford. The baculovirus expression vector system uses insect cells to produce protein, and it is the first non-mammalian expression system that has been used successfully to generate functional full-length HST proteins. See Ali et al. (1996), *Biochem. J.* 319:101–105. The baculovirus expression method of Ali et al. (1996) produced a high-yield of functionally active HST (>20 mg/L), and this general method will be utilized for expression and purification of the novel recombinant transferrins described herein.

The baculovirus transfer vector pBacPAK8 (Clontech Laboratories Inc., Palo Alto, Calif.) would be used to subclone the native HST. The pBacPAK8 plasmid contains the strong polyhedrin promoter for expression of the HST gene. Recombinant baculovirus is generated with the BacPAK baculovirus expression system (Clontech) by using the HIGH FIVE host insect cells line (BTI TN 5B1-4; Invitrogen Corp., San Diego, Calif., USA).

G. Insertion of Designed Peptides at Codons 289 and 279:

The insertion of the designed peptides after codons 289 and 279 in the N-terminal lobe of human serum transferrin can be performed using the standard molecular biology technique known as "cassette mutagenesis." A region of the baculovirus expression system plasmid containing HST would be amplified via PCR using primers which contain the desired insertion sequence. For instance, to produce a recombinant HST that contains the Mut. 1 peptide sequence inserted at codon 289, one could amplify the HST gene via PCR with the following two primers:

Primer #1: 5'-tta-att-gaa-ttc-caa-cta-ttc-agc-tct-cct-gtt-tct-cag-aac-tac-gtc-atc-gtc-ctc-cgc-ggc-gat-gtt-tct-cag-aac-tac-gtc-act-gtc-ctccat-ggg-aag-gac-ctg-ctg-ttt-3' and Primer #2:5'-ccc-tac-act-gtt-aac-act-cca-ctc-3'. The codons encoding the amino acids of the Mut.1 peptide insertion sequence are underlined above and the surrounding codons code for the normal amino acids found in the HST sequence around codon 289. The amplified fragment resulting from the PCR reaction would be digested with EcoRI and HpaII restriction enzymes since the primers contain these sites (italics, bold). The digested fragment would then be cloned into the vector containing HST via the EcoR1 and HpaII restriction sites. Codon selection in the primers above was made with attention to codon usage efficiency in humans; see Sharp et al. (1988) *Nucleic Acids Research* 16:8207. The insertion of the inventive peptides at codon 279 would follow the same procedures as described above with one designing primers that contain DNA encoding the peptide to be inserted as well as several normal HST codons around and including codon 279. The oligonucleotides (primers) for all procedural PCR reactions needed may be selected so that the annealing regions possessed a melting point of approximately 60–70 degrees Celsius, according to standard molecular biology methodology.

H. Insertion of the Designed Peptides at Codons 33, 75, and 257:

The insertion of the proposed peptides after codons 33, 75, and 257 in the N-terminal lobe of HST can be performed using the PCR-ligation-PCR mutagenesis procedure developed by Ali et. al. See e.g. Ali, S. A. and Steinkasserer, A. (1995) *Bio Techniques* 18:746–750; Ali, S. A. and Steinkasserer, A. (1997) in *Gene Cloning and Analysis: Current Innovations* (Schaefer, B., ed) pp. 133–145, Horizon Scientific Press Ltd., Wymondham, United Kingdom; Ali, S. et al. (1997) *Bio Techniques* 22:1060–1062. This procedure can be best understood by referring to FIG. 4. One first designs two pairs of primers containing the DNA sequences encoding the peptide that is to be inserted into HST. Then one performs two PCR reactions. In one PCR reaction the A1/A2 primer set is used. The A1 primer begins with the first codons of HST while the A2 primer contains DNA sequence which encodes part of the peptide insert as well as sequence homologous to codons in the region where the peptide is to be inserted. In this way the A1/A2 PCR reaction amplifies part of the HST gene along with part of the DNA encoding the peptide to be inserted. The other PCR reaction utilizes the B1/B2 set of primers. The B2 primer begins with the last codon of HST while the B1 primer contains the remainder of the DNA sequence required to encode the peptide insert as well as required sequence needed to amplify the remaining HST gene segment flanked by the B1 and B2 primers. Thus, in the PCR-ligation-PCR mutagenesis procedure, the HST gene is first amplified as two different halves which each include a piece of the insert. Then, the two halves of HST produced with the first two PCR reactions are phosphorylated with T4 polynucleotide kinase and ligated (connected) with T4 DNA ligase, producing a complete gene encoding the HST protein along with one of the proposed peptides after either codon 33, 75, or 257 depending on the primer selected. Finally, this recombinant gene is amplified with another PCR reaction using primers A1 and B2 which completely flank the gene of interest. In this way, any of the four proposed peptides (Mut. 1–4) can be inserted in the surfaced exposed N-terminal loops of HST after codons 33, 75, or 257.

I. Expression and Purification of Recombinant Human Serum Transferrins:

The plasmid containing the recombinant HST gene along with viral DNA (BacPAK6: linearized replication-deficient recombinant baculovirus DNA derived from the nuclear polyhedrosis virus, *Autographia californica*) would be cotransfected via lipofection into host cells, and the recombinant baculovirus would be isolated, expanded in suspension cultures, and titrated with standard methodology. See O'Reilly, D. R. et al. (1994) *Baculovirus Expression Vectors: A Laboratory Manual,* Oxford University Press, Oxford; Ali, S. et al. (1996) *Biochem. J.* 319:191–195. The HIGH FIVE cell cultures is grown at 27° C. in SF900II serum-free medium (Life Technologies G.m.b.H., Berlin, Germany) with added 1 mM glutamine, 100 units/mL streptomycin, and 100 μg/mL penicillin. An additional supplement of 10 units/mL heparin (sodium salt: grade 1-A from porcine intestinal mucosa) is then added to suspension cultures, and the cultures then shaken at 80 rev./min. After infection, the recombinant HST can be purified from expression culture supernatants using hydrophobic interaction chromatography with a Phenyl-Sepharose column as described by Ali et al. (1999) *J. Biol. Chem.* 274:34 24066–24073. Purified protein may be analyzed with SDS-PAGE and Western Blot analysis using a rabbit anti-HST antibody or an immune serum raised against the inserted peptide.

J. Addition of Membrane Targeting Signal:

As it is likely that most HIV-1 protease activity is found at the membrane, the addition of a membrane targeting signal to the proposed recombinant human serum transferrins, which contain apoptotic RGD peptides inserted into surface exposed loops of the N-terminal lobe, will increase the efficacy of the invention described herein. The membrane targeting signal localizes the recombinant human serum transferrin molecule to the membrane and in this way increases the likelihood that the recombinant HST undergoes cleavage via an HIV-1 protease enzyme.

The final ten C-terminal amino acids of the $p21^{H\text{-}ras}$ protein confer membrane localization upon the protein, and this sequence has been attached to the C-terminus of other proteins with the same effect. Thus, the inventive recombinant human serum transferrins described herein are further modified by adding the last ten C-terminal amino acids of $p21^{H\text{-}ras}$ to their C-termini. The C-terminus of a protein can be thought of as the tail end of a protein; proteins are synthesized from N-terminus to C-terminus. One can attach the final ten C-terminal amino acids of $p21^{H\text{-}ras}$ to the C-terminal tail of the proposed recombinant human serum transferrins by using standard PCR mutagenesis. Two primers which flank the recombinant HST gene are to be structured for this process: one primer (the forward primer) contains DNA with sequence homology to the N-terminal coding region of the recombinant HST gene while the other primer (the reverse primer) contains DNA with sequence homology to the C-terminal coding region of the recombinant HST gene as well as DNA sequence coding for the last ten C-terminal amino acids of $p21^{H\text{-}ras}$.

Thus, like any standard PCR, the forward primer is complimentary to the front of the gene while the reverse primer is complimentary to the back of the gene. Furthermore, both primers may contain restriction sites to permit subcloning. Yet, in this PCR mutagenesis insertion reaction, the reverse primer has extra codons which encode the last ten C-terminal amino acids of the $p21^{H\text{-}ras}$ protein. The PCR reactions may use a plasmid containing a recombinant HST gene as a template. Although the reverse primer in this PCR mutagenesis reaction has some which are not complimentary to the HST gene, the primer will still anneal, and the PCR reaction will lead to a recombinant HST gene containing DNA at its 3' end which codes for the last ten C-terminal amino acids of $p21^{H\text{-}ras}$. The PCR fragment would be digested with restriction enzymes that recognize the sequences designed in the primers and would be cloned into a vector previously digested with the same restriction enzymes.

Expression of the cloned gene then yields a recombinant HST containing one of the proposed peptides inserted into a surface exposed N-terminal loop along with ten membrane-targeting amino acids (the last ten amino acids of the $p21^{H\text{-}ras}$) at the C-terminal tail end of the HST protein. In this way membrane localization is conferred to each recombinant HST described herein, and this modification should significantly improve the anticipated therapeutic efficacy of the recombinant proteins. The same pair of primers could be used to add the ten $p21^{H\text{-}ras}$ membrane targeting amino acids to the C-terminus of every recombinant HST, for the different recombinant HST proteins described herein do not differ at their initial N-terminal and C-terminal amino acids (the recombinant HST proteins only differ internally by which peptide insert was chosen and which internal surface exposed loop was chosen).

Restriction enzymes used herein can be purchased from New England Biolabs (Beverly, Mass.). Oligonucleotides can be obtained from Operon Technologies Incorporated (Alameda, Calif.). The BacPAK baculovirus expression system can be purchased from CLONTECH (Palo Alto, Calif.). The plasmid TFR27A containing the HST gene can be obtained from American Type Cell Culture (A.T.C.C., catalogue #53106, Rockville, Md.). T4 DNA ligase, DNA Polymerase I (Klenow fragment), and T4 polynucleotide kinase can be purchased from Pharmacia-PL Biochemicals. SF900II serum-free medium is available from Life Technologies G.m.b.H. (Berlin, Germany). Heparin (sodium salt: grade 1-A from porcine intestinal mucosa) can be obtained from Sigma-Aldrich Handels G.m.b.H., Vienna, Austria.

K. The Effects Obtained and Range of Alternatives:

Those in the art will appreciate that the use of a natural transport protein such as human serum transferrin for drug delivery is very promising. A conjugate of human serum transferrin and a genetic mutant of diphtheria toxin was recently used to treat recurrent malignant brain tumors in humans. Complete remission was observed in two of fifteen patients and nine showed a 50% reduction is tumor size. See Laske, D. W. et al. (1997) *Nature Medicine* 3:12 1362–1368. Yet proteins conjugated to transferrin have been shown to induce an antibody response. See Ali, S. et al. (1999) *FEBS Letters* 459, 230–232. A better alternative for drug delivery via the transferrin pathway appears to be the recent and novel use of human serum transferrin as a carrier protein. See Ali, S. (1999) *J. Biol. Chem.* 274:34 24066–24073. The concealed peptide in the structure of transferrin provides a way of escaping the immune response which is notoriously problematic when using peptide drugs. In other instances insertion of a peptide sequence into a loop of human serum transferrin has also been shown not to elicit an immune response while the same insert when conjugated to transferrin did elicit a response. See Ali, S. et al. (1999) *FEBS Letters* 459:230–232.

The transferrin pathway is also favorable because hijacking the receptor-mediated endocytosis pathway of transferrin ensures that the peptide can be brought into cells. In the past peptide drugs were often ineffective for lack of an efficient crossing mechanism of the biological plasma membrane. Furthermore, hiding the peptide in the human serum transferrin molecule overcomes problems of solubility often encountered when using peptide drugs. Also, the transferrin carrier protein can protect the peptide from degradation until it has reached the site of action.

The transferrin pathway is also very attractive as HIV infected cells and tumor cells express upregulated transferrin receptors while normal resting human cells do not require much iron for healthy function and do not express detectable transferrin receptors on their membranes. Finally, transferrin has a long circulatory half-life, it is able to cross the blood-brain barrier, and there are no described toxic effects of transferrin. The inventive recombinant human serum transferrin combines the recent example of HST as a potential carrier protein with the known HIV-1 protease specificity and a small apoptotic peptide.

The use of apoptotic peptides as opposed to noncellular toxins is a better way to cause cell death as apoptotic peptides derived from self-proteins are not recognized as foreign. Thus the recombinant proteins disclosed herein retain biological activity, act as competitive HIV-1 protease substrates, and selectively cause apoptosis in HIV-1 infected cells. While disclosed herein in association with HIV-1 infection mechanisms, the same general construct may be also effective for other classes of non-immunogenic antitumor drugs.

Obviously, many modifications and variations can be effected without departing from the spirit of the invention disclosed herein. It is therefore intended that the scope of the invention be determined solely by the claims appended hereto.

It is claimed:

1. A recombinant human serum transferrin useful in inducing apoptosis in HIV-1 infected cells, wherein:
a peptide including an amino acid motif selected to induce apoptosis is inserted into the surface exposed loops of the N-terminal lobe of said human serum transferrin.

2. A recombinant human serum transferrin according to claim 1, wherein:
said inserted peptide includes the amino acid RGD apoptotic motif.

3. A recombinant human serum transferrin according to claim 2, wherein:
said inserted peptide further includes a modified p17/p24 cleavage site
VSQNYVIVL.

4. A recombinant human serum transferrin according to claim 1, wherein:
a membrane targeting signal comprising one or more of the membrane targeting acids
$p21^{H\text{-}ras}$ is attached to the C-terminus of said human serum transferrin.

5. A recombinant human serum transferrin according to claim 4, wherein:
said inserted peptide includes the amino acid RGD apoptotic motif.

6. A recombinant human serum transferrin according to claim 5, wherein:
said inserted peptide further includes a modified p17/p24 cleavage site
VSQNYVIVL.

7. A recombinant human serum transferrin according to claim 1, wherein:
said inserted peptide is selected from the group consisting of the following group of peptides:
SEQ. ID No. 1; SEQ. ID No. 2; SEQ. ID No. 3; and SEQ. ID No. 4.

8. A recombinant human serum transferrin according to claim 7, wherein:
a membrane targeting signal comprising one or more of the membrane targeting acids
$p21^{H\text{-}ras}$ is attached to the C-terminus of said human serum transferrin.

9. A recombinant human serum transferrin according to claim 1, wherein:
said peptide is inserted in the surface exposed loops of said N-terminal lobe at one or more of the following codons:
32–33; 74–75; 256–257; 279–280; or 288–289.

10. A recombinant human serum transferrin according to claim 9, wherein:
said inserted peptide is selected from the group consisting of the following group of peptides:
SEQ. ID No. 1; SEQ. ID No. 2; SEQ. ID No. 3; and SEQ. ID No. 4.

11. A recombinant human serum transferrin according to claim 10, wherein:
a membrane targeting signal comprising one or more of the membrane targeting acids
$p21^{H\text{-}ras}$ is attached to the C-terminus of said human serum transferrin.

12. A method for treating HIV-1 infection in humans comprising the steps of:
altering the protein structure of human serum transferrin by inserting into the surface exposed loops of the N-terminal lobe of said transferrin an apoptosis inducing peptide flanked by HIV-1 protease cleavage sites;
replicating said altered human serum transferrin; and
introducing said replicated altered human serum transferrin into an HIV-1 infected human.

13. A method according to claim 12, wherein:
said step of altering said transferrin includes the step of inserting said apoptosis inducing peptide includes the further step of selecting said peptide from the group consisting of:
SEQ. ID No. 1; SEQ. ID No. 2; SEQ. ID No. 3; and SEQ. ID No. 4.

14. A method according to claim 13, wherein:
said step of altering said transferrin includes the step of inserting said peptide in the surface exposed loops of said N-terminal lobe at one or more of the codons 32–33; 74–75; 256–257; 279–280; or 288–289.

* * * * *

SEQUENCE LISTING

```
<160> NUMBER OF SEQ ID NOS: 4

<210> SEQ ID NO 1
<211> LENGTH: 21
<212> TYPE: PRT
<213> ORGANISM: Artificial Sequence
<220> FEATURE:
<223> OTHER INFORMATION: The designed peptide contains a central RGD
      motif flanked by two modified p17/p24 HIV-1 protease
      cleavage sites that release the RGD-containing
      peptide sequence.  The peptide insertion site is
      the surface exposed loops of the N-terminal lobe
``` of human serum transferrin (HST) at codons 32-33,
74-75, 256-257, or 288-289.

<400> SEQUENCE: 1

Val Ser Gln Asn Tyr Val Ile Val Leu Arg Gly Asp Val Ser Gln Asn
 1               5                  10                  15

Tyr Val Ile Val Leu
            20

<210> SEQ ID NO 2
<211> LENGTH: 22
<212> TYPE: PRT
<213> ORGANISM: Artificial Sequence
<220> FEATURE:
<223> OTHER INFORMATION: The designed peptide contains a central RGD
      motif flanked by two modified p17/p24 HIV-1 protease
      cleavage sites that release the RGD-containing
      peptide sequence. The peptide insertion site is
      the surface exposed loops of the N-terminal lobe
      of human serum transferrin (HST) at codons 32-33,
      74-75, 256-257, or 288-289.

<400> SEQUENCE: 2

Val Ser Gln Asn Tyr Val Ile Val Leu Arg Gly Asp Ser Val Ser Gln
 1               5                  10                  15

Asn Tyr Val Ile Val Leu
            20

<210> SEQ ID NO 3
<211> LENGTH: 22
<212> TYPE: PRT
<213> ORGANISM: Artificial Sequence
<220> FEATURE:
<223> OTHER INFORMATION: The designed peptide contains a central RGD
      motif flanked by two modified p17/p24 HIV-1 protease
      cleavage sites that release the RGD-containing
      peptide sequence. The peptide insertion site is
      the surface exposed loops of the N-terminal lobe
      of human serum transferrin (HST) at codons 32-33,
      74-75, 256-257, or 288-289.

<400> SEQUENCE: 3

Val Ser Gln Asn Tyr Val Ile Val Leu Gly Arg Asp Pro Val Ser Gln
 1               5                  10                  15

Asn Tyr Val Ile Val Leu
            20

<210> SEQ ID NO 4
<211> LENGTH: 24
<212> TYPE: PRT
<213> ORGANISM: Artificial Sequence
<220> FEATURE:
<223> OTHER INFORMATION: The designed peptide contains a central RGD
      motif flanked by two modified p17/p24 HIV-1 protease
      cleavage sites that release the RGD-containing
      peptide sequence. The peptide insertion site is
      the surface exposed loops of the N-terminal lobe
      of human serum transferrin (HST) at codons 32-33,
      74-75, 256-257, or 288-289.

<400> SEQUENCE: 4

Val Ser Gln Asn Tyr Val Ile Val Leu Gly Arg Gly Asp Ser Pro Val
 1               5                  10                  15

Ser Gln Asn Tyr Val Ile Val Leu
            20